United States Patent
Grodzki et al.

(10) Patent No.: US 12,007,457 B2
(45) Date of Patent: Jun. 11, 2024

(54) ACTUATING A MAGNETIC RESONANCE DEVICE WITH SATURATION

(71) Applicant: Siemens Healthcare GmbH, Erlangen (DE)

(72) Inventors: David Grodzki, Erlangen (DE); Thorsten Speckner, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/957,004

(22) Filed: Sep. 30, 2022

(65) Prior Publication Data

US 2023/0098129 A1    Mar. 30, 2023

(30) Foreign Application Priority Data

Sep. 30, 2021    (DE) .......................... 102021210969.1

(51) Int. Cl.
*G01R 33/48*    (2006.01)
*A61B 5/055*    (2006.01)
*G01R 33/56*    (2006.01)

(52) U.S. Cl.
CPC .............. *G01R 33/48* (2013.01); *A61B 5/055* (2013.01); *G01R 33/5608* (2013.01)

(58) Field of Classification Search
CPC ...... G01R 33/48; G01R 33/5608; A61B 5/055
See application file for complete search history.

(56) References Cited

U.S. PATENT DOCUMENTS

| | | | |
|---|---|---|---|
| 2013/0009640 A1 | 1/2013 | Fautz et al. | |
| 2015/0362578 A1* | 12/2015 | Biber | G01R 33/3875 324/309 |
| 2016/0169997 A1* | 6/2016 | Fautz | G01R 33/543 324/309 |
| 2021/0278492 A1 | 9/2021 | Grodzki et al. | |
| 2021/0298628 A1* | 9/2021 | Jin | G01R 33/445 |

FOREIGN PATENT DOCUMENTS

DE    102011078680 B3    12/2012
DE    102020202830 A1    9/2021

* cited by examiner

*Primary Examiner* — Gregory H Curran
(74) *Attorney, Agent, or Firm* — Banner & Witcoff Ltd.

(57) ABSTRACT

A method for actuating a magnetic resonance system having a radiofrequency unit designed to generate a radiofrequency pulse for the saturation of nuclear spins in an area under examination of an object under examination. The method includes loading a B0 map of the magnetic resonance system; loading frequency information on nuclear spins to be saturated in the area under examination; ascertaining at least one global RF saturation pulse for the global saturation of the nuclear spins to be saturated on the basis of the B0 map and the frequency information; and outputting the RF saturation pulse via the radiofrequency unit of the magnetic resonance system.

9 Claims, 2 Drawing Sheets

ACTUATING A MAGNETIC RESONANCE DEVICE WITH SATURATION

TECHNICAL FIELD

The disclosure relates to a method for actuating a magnetic resonance device by outputting a saturation pulse.

BACKGROUND

Magnetic resonance technology (the abbreviation MR below stands for magnetic resonance) is a known technology with which images of the interior of an object under examination can be generated. In simplified terms, for this purpose the object under examination is positioned in a magnetic resonance device in a comparatively strong static, homogeneous main magnetic field, also called a B0 field, with field strengths of 0.2 tesla to 7 tesla and more, so that its nuclear spins are oriented along the constant magnetic field. To trigger nuclear spin resonances that can be measured as signals, radiofrequency excitation pulses (RF pulses) are irradiated into the object under examination, the triggered nuclear spin resonances are measured as what is known as k-space data and on the basis thereof MR images are reconstructed or spectroscopy data is ascertained. RF pulses typically correspond to a magnetic alternating field. For position encoding of the measurement data rapidly switched magnetic gradient fields, called gradients for short, are superimposed on the constant magnetic field. A diagram used that describes a sequence over time of RF pulses to be irradiated and of gradients to be switched is referred to as a pulse sequence (diagram), or else as a sequence for short. The measurement data plotted is digitized and stored as complex numerical values in a k-space matrix. An associated MR image can be reconstructed from the k-space matrix populated with values, e.g. by means of a multidimensional Fourier transform.

The intensity of MR signals is a function of the area surrounding the nuclear spins, in particular the molecules that comprise the nuclear spins. This produces a contrast in the reconstructed image data, wherein fat for example has a different signal intensity from water, of which for example there is a preponderance in muscle tissue. The suppression of signals emanating from a particular tissue, also called saturation, is a common technique in magnetic resonance imaging. In this case the saturation can take place spectrally, wherein the chemical shift between nuclear spins in different tissues is exploited: as a function of the surrounding tissue, nuclear spins have a different resonance frequency, i.e. a Larmor frequency in relation to the strength of the main magnetic field. First of all an RF saturation pulse is output, i.e. an RF pulse with a small frequency bandwidth for the resonant excitation of nuclear spins to be saturated that are bound in a defined tissue, said nuclear spins dephasing in the defined tissue, before RF pulses and gradient fields are output for the generation of desired MR signals that are to be measured. The RF saturation pulses have a frequency band such that nuclear spins bound in a different tissue are to a great extent not excited. The only nuclear spins that contribute to the MR signals for the imaging are then those that are situated outside the frequency band of the RF saturation pulses. The spectral saturation is in particular a function of the homogeneity of the main magnetic field and of the tissue to be suppressed, in other words to be saturated.

SUMMARY

An object of the disclosure is to make imaging in a magnetic resonance tomography system using RF saturation pulses better and more cost-effective.

This object is achieved by a method for actuating a magnetic resonance system comprising a radiofrequency unit designed to generate a radiofrequency pulse (RF pulse) for the saturation of nuclear spins in an area under examination of an object under examination, a magnetic resonance system, a computer program, and an electronically readable data storage medium.

A disclosed method for actuating a magnetic resonance system comprising a radiofrequency unit designed to generate a radiofrequency pulse for the saturation of nuclear spins in an area under examination of an object under examination comprises the steps:

loading a B0 map of the magnetic resonance system,
loading frequency information on nuclear spins to be saturated in the area under examination,
ascertaining at least one global RF saturation pulse for the global saturation of the nuclear spins to be saturated on the basis of the B0 map and the frequency information,
outputting the RF saturation pulse via the radiofrequency unit of the magnetic resonance system.

Image data should be generated, typically as part of a magnetic resonance examination, for an area of the object under examination, the area under examination. The object under examination is typically a patient. The area under examination typically comprises a section of the object under examination.

The frequency information makes it possible to determine a Larmor frequency of the nuclear spins to be saturated in their chemical bond (in their tissue), at which the nuclear spins are resonantly excited. The Larmor frequency is a product of the gyromagnetic ratio of a nuclear spin and the strength of the magnetic field surrounding the nuclear spin. The magnetic field surrounding the nuclear spin results to a great extent from the main magnetic field, which however is modulated because of the chemical environment of the nuclear spin, in particular of the tissue surrounding the nuclear spin. The modulation is quantified using the chemical shift, which for example between fat and water is approximately 3.4 ppm. The frequency information can for example comprise a gyromagnetic ratio, if appropriate with associated chemical shift, applicable for nuclear spins to be saturated. The main magnetic field itself can have local variations. The main magnetic field can also be referred to as a B0 field. The loaded B0 map indicates the strength of the main magnetic field in a spatial resolution.

A B0 map for a magnetic resonance system can be stored on a storage medium, which is accessed in the course of the loading procedure. In this case it is already sufficient if the B0 map has been measured once only, e.g. during the installation of the magnetic resonance system. The measurement of a B0 map can take place e.g. by means of a field camera or by means of an MR measurement or the B0 map can be ascertained by simulation.

Frequency information for different nuclear spins to be saturated can be stored on a storage medium, which is accessed in the course of the loading procedure.

RF pulses generally have a frequency bandwidth around a basic frequency and are consequently emitted in a frequency band, defined by the basic frequency and the frequency bandwidth. The basic frequency corresponds to the frequency of the RF pulse, in other words the carrier frequency. An RF pulse causes a resonant excitation of a substance, providing the Larmor frequency of a nuclear spin comprised by the substance, in other words the resonance frequency of the substance, corresponds to the frequency of the radiofrequency pulse, in particular at the position of the nuclear spin. An RF pulse can cause an excitation of a substance, providing the Larmor frequency of a nuclear spin comprised by the substance is included by the frequency band of the RF pulse.

A substance can for example be a molecule, a combination of different molecules, and/or a tissue. A substance can also be a further structure that is not explicitly cited here, and is not restricted to the cited examples.

An RF pulse designed for a spectrally selective excitation of nuclear spins of a tissue typically has a frequency band that includes the resonance frequency of these nuclear spins.

An RF saturation pulse designed for a spectrally selective excitation of nuclear spins to be saturated on the basis of a loaded B0 map of a magnetic resonance system to be used is typically ascertained such that a local influence, emanating from local changes in the main magnetic field, on the resonance frequency of the nuclear spins to be saturated, in particular a local modulation of the resonance frequency, is ascertained and/or taken into consideration on the basis of the B0 map.

By ascertaining a global RF saturation pulse in accordance with the disclosure on the basis of loaded frequency information and a loaded B0 map it is possible to create RF saturation pulses system-specifically, i.e. specifically for a magnetic resonance system used. The ascertained RF saturation pulses are global and nevertheless achieve a spatially adjusted saturation of the desired nuclear spins. This can preferably take place once only, e.g. on startup of the magnetic resonance system, so that during subsequent operation stored RF saturation pulses can be accessed, which makes the operation stable, and as a result of which computing times and other computing effort for a subsequent calculation can be saved.

A disclosed magnetic resonance system comprises a magnet unit, a gradient unit, a radiofrequency unit and a control device with a saturation pulse determination unit designed to carry out a method in accordance with aspects of the disclosure.

A disclosed computer program implements a disclosed method on a control device when it is executed on the control device.

The computer program can in this case also be present in the form of a computer program product, which can be loaded directly into a memory of a control device, containing program code means in order to execute an disclosed method when the computer program product is executed in the computing unit of the computing system.

A disclosed electronically readable data storage medium comprises electronically readable control information stored thereon, which comprises at least one disclosed computer program and is configured such that when the data storage medium is used in a control device of a magnetic resonance system it carries out a disclosed method.

The advantages and explanations specified in relation to the method also apply analogously for the magnetic resonance system, the computer program product and the electronically readable data storage medium.

DESCRIPTION OF THE DRAWINGS

Further advantages and details of the present disclosure emerge from exemplary embodiments described below and on the basis of the drawings. The examples given do not represent a restriction of the disclosure. In the drawings.

DETAILED DESCRIPTION

Figure 1:
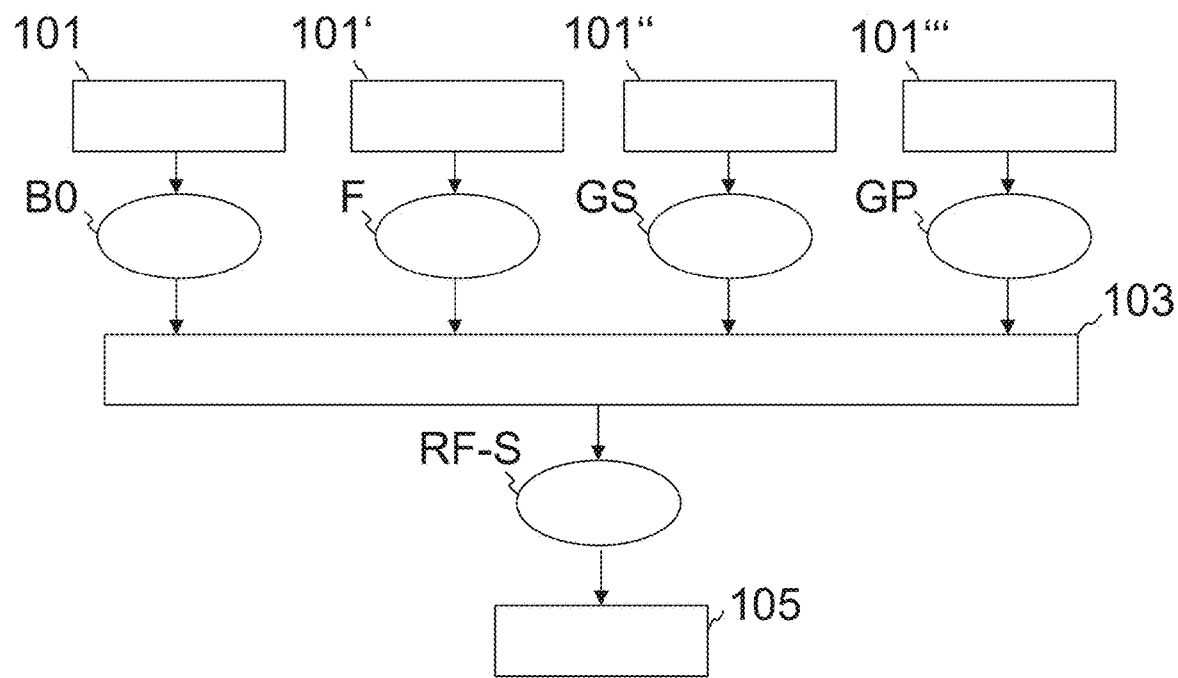
FIG. 1 shows a schematic flow chart of a method in accordance with aspects of the disclosure.

FIG. 1 is a schematic flow chart of a disclosed method for actuating a magnetic resonance system comprising a radiofrequency unit 7 designed to generate a radiofrequency pulse for saturation of nuclear spins in an area under examination of an object under examination.

A B0 map B0 of the magnetic resonance system is loaded (Block 101). This can in this case be determined once only, e.g. during installation of the magnetic resonance system, and loaded from a memory. In this way the system-specific B0 map, which describes static deviations of the main magnetic field of the magnetic resonance system from an ideal, homogeneous main magnetic field, is rapidly available.

Frequency information F on nuclear spins to be saturated in the area under examination is loaded (Block 101'). Frequency information for nuclear spins to be saturated, e.g. nuclear spins bound in different tissues, can likewise already be present in stored form and can be loaded from a memory, in which e.g. a list of possible nuclear spins to be saturated is stored with associated frequency information F. The frequency information F can be measured or based on values found in the literature.

At least one global RF saturation pulse RF-S for the global saturation of the nuclear spins to be saturated is ascertained on the basis of the B0 map B0 and of the frequency information F (Block 103). In this case the RF saturation pulse RF-S is ascertained such that when it is irradiated into an object under examination in the magnetic resonance system, it compensates for static deviations in the main magnetic field. An ascertained RF saturation pulse RF-S causes an excitation of the nuclear spins to be saturated in an area under examination situated in the imaging volume of the magnetic resonance system.

The ascertained RF saturation pulse RF-S is output via the radiofrequency unit 7 of the magnetic resonance system (Block 105).

Furthermore, gradient-exemplar-specific higher-order disturbance terms GS can be loaded (Block 101"), which are taken into consideration when ascertaining global RF saturation pulses. Gradient-exemplar-specific disturbance terms can be measured once only, e.g. on startup of the magnetic resonance system, in particular in the course of a test measurement (tune-up), and loaded from a memory. Gradient-exemplar-specific disturbance terms typically describe dynamic changes in the magnetic field that arise as a result of switching of gradient coils in the various directions (x,y,z) and are thus location-dependent and time-dependent variables $GS(x,y,z,t)$. By taking gradient-exemplar-specific disturbance terms into consideration the ascertained RF saturation pulses can also compensate for dynamic changes in the magnetic field.

A protocol GP planned for an MR measurement can be loaded (Block 101'''), from which, when global RF saturation pulses are ascertained, parameters, in particular planned gradient fields, of the planned protocol are taken into consideration. A planned protocol is here in particular a pulse sequence, with associated parameters, used during a desired MR measurement, in which a disclosed RF saturation pulse is to be employed.

Loading planned protocols can include at least one instance of loading gradient fields to be switched in accordance with the planned protocol, so that when the global RF saturation pulse is ascertained the gradient fields to be switched are taken into consideration.

An RF saturation pulse RF-S ascertained by taking into consideration planned protocols and/or gradients GP to be switched can thus be referred to as a protocol-specific RF saturation pulse RF-S. To this end it is possible, e.g. on the basis of gradient-exemplar-specific disturbance terms GS and a planned protocol GP, to determine a protocol-specific field distribution, in that for each protocol a characteristic time t_c is used which is inserted as a time value into the gradient-exemplar-specific disturbance terms GS: GS(x,y,z, t_c). The characteristic time t_c can also be stored for each protocol and either calculated on the basis of the associated pulse sequence topology, in particular the gradients thereof to be switched, or can be established by the protocol developer on the basis of heuristics. A parameter of the protocol to be taken into consideration when ascertaining RF saturation pulses RF-S can thus be a characteristic time t_c. The protocol-specific field distribution can easily be taken into consideration during the ascertainment of the RF saturation pulses.

Such protocol-specific RF saturation pulses, that were ascertained by taking planned protocols into consideration, can be ascertained once only for each planned protocol and stored, e.g. together with the protocol. Protocol-specific RF saturation pulses can thus be ascertained in a manner that is intensive in terms of computing time prior to the performance of an MR measurement using the protocol, as a result of which computing capacities are kept free during the MR measurement.

In this way ascertained RF saturation pulses can also compensate for dynamic deviations in the main magnetic field.

Further measures stabilizing the main magnetic field B0 of a magnetic resonance system, such as e.g. shimming, can additionally be employed, wherein shim parameters employed are to be taken into consideration while ascertaining the RF saturation pulses.

In accordance with the disclosure an RF saturation pulse is thus ascertained, which is adjusted in terms of time and space to static and if appropriate dynamic magnetic field changes contingent upon various system-specific causes.

Figure 2:
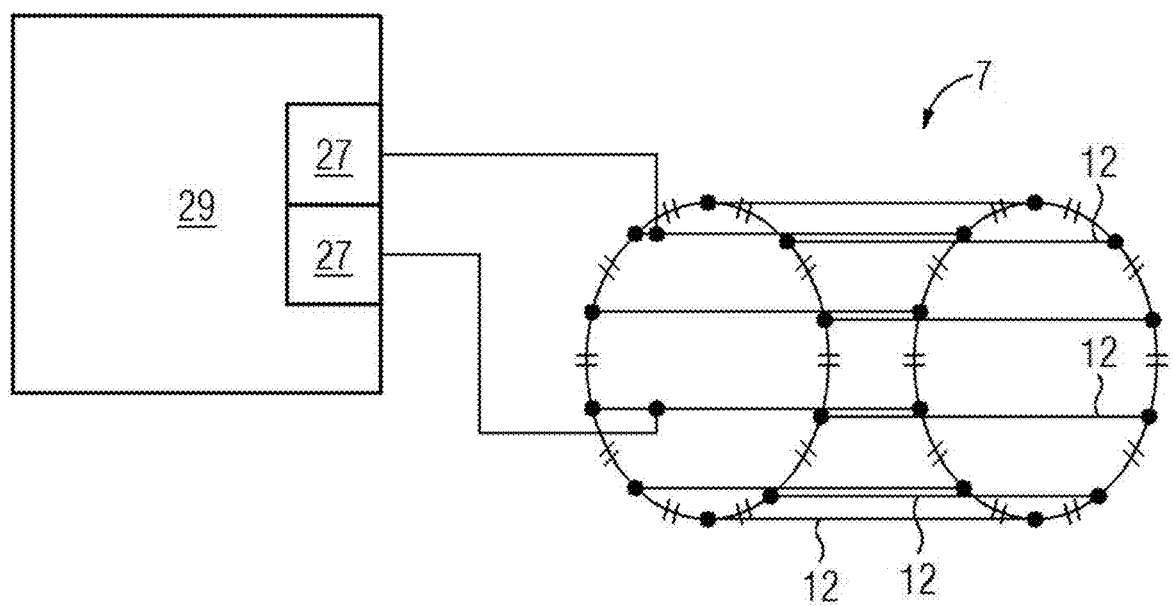
FIG. 2 shows a schematic representation of a radiofrequency unit of a magnetic resonance system in accordance with aspects of the disclosure.

FIG. 2 shows a radiofrequency unit 7 in a schematic representation of one possible form of embodiment. The radiofrequency unit 7 comprises at least two transmission elements 12 connected to form a radiofrequency antenna unit and is connected to a radiofrequency antenna control unit 29. In accordance with this form of embodiment the radiofrequency antenna control unit 29 comprises a plurality of transmission channels 27, preferably at least two transmission channels 27. In accordance with this form of embodiment the transmission channels 27 feed a plurality of the transmission elements 12 of the radiofrequency unit.

The radiofrequency antenna control unit 29 can also comprise just one transmission channel 27. The radiofrequency unit 7 can comprise one transmission element 12 or a plurality of transmission elements 12, which are fed by in each case precisely one independent transmission channel 27.

In FIG. 2 just two independent transmission channels 27 are shown for the sake of clarity, and are directly in signal connection with two of the transmission elements 12. The further transmission elements 12 are also fed by these using a capacitive or inductive coupling. Normally it is possible to use an actuation of the radiofrequency unit 7 such as this to generate various elliptical polarizations with a corresponding spatial amplitude distribution. As the number of transmission elements 12 fed independently by various transmission channels 27 increases, so does the number of degrees of freedom to adjust the spatial component of the field distribution more finely.

The transmission channels 27 are here for example supplied by the radiofrequency antenna control unit 29, which for example is part of a radiofrequency transceiver controller 7', with data on the RF saturation pulse to be emitted, for example via a signal bus, and the time coordination with the gradients or the pulse sequence is controlled.

The radiofrequency antenna unit of the radiofrequency unit 7 formed from the transmission elements 12 can be designed as a body coil of a magnetic resonance system. A local coil with an array of antenna coils is for example also conceivable instead of the body coil. In contrast to the body coil, in this case the effective areas of the individual antenna coils are significantly less coupled or in the case of antenna coils further remote from one another are completely disjunct, so that the spatial distribution is governed primarily by the position of the antenna coil and less by interference with the signals of the other antenna coils.

Figure 3:
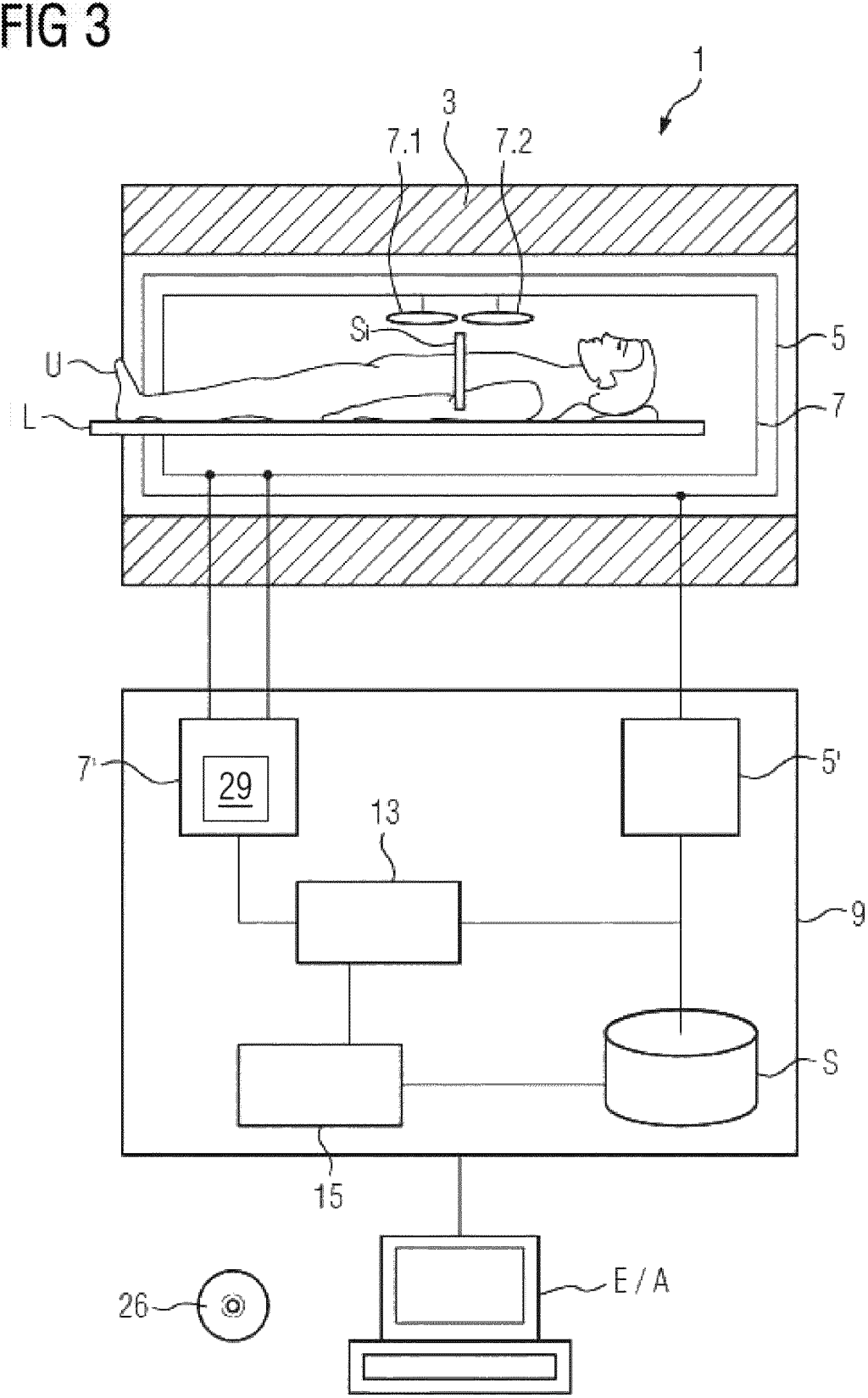
FIG. 3 shows a schematically represented magnetic resonance system in accordance with aspects of the disclosure.

FIG. 3 schematically represents a magnetic resonance system 1 in accordance with aspects of the disclosure. This comprises a magnet unit 3 for generating the constant magnetic field, a gradient unit 5 for generating the gradient fields, a radiofrequency unit 7 for irradiation and for receiving radiofrequency signals and a control device 9 designed for the performance of a method in accordance with aspects of the disclosure.

In FIG. 3 these subunits of the magnetic resonance system 1 are represented schematically only roughly. In particular the radiofrequency unit 7 can consist of multiple subunits, for example of multiple coils such as the schematically shown coils 7.1 and 7.2 or more coils, which can be configured either just to transmit radiofrequency signals or just to receive the triggered radiofrequency signals or for both. The radiofrequency unit 7 is preferably a radiofrequency unit 7 as is described with reference to FIG. 2.

To examine an object under examination U, for example a patient or else a phantom, the latter can be introduced into the imaging volume of the magnetic resonance system 1 on a couch L. The slice or the slab $S_i$ represents an exemplary target volume of the object under examination, from which echo signals are to be recorded and captured as measurement data.

The control device 9 serves to control the magnetic resonance system 1 and can in particular control the gradient unit 5 by means of a gradient controller 5' and the radiofrequency unit 7 by means of a radiofrequency transceiver controller 7'. The radiofrequency unit 7 can here comprise multiple channels, on which signals can be transmitted or received.

The radiofrequency unit 7 is responsible, together with its radiofrequency transceiver controller 7', for the generation and irradiation (transmission) of a radiofrequency alternating field for manipulation of the spins in an area to be manipulated (for example in slices S to be measured) of the object under examination U. In this case the center frequency of the radiofrequency alternating field, also referred to as the B1 field, is generally wherever possible set such that it lies close to the resonance frequency of the spins to be manipulated. Deviations between the center frequency and the resonance frequency are referred to as off-resonance. To generate the B1 field currents controlled by means of the radiofrequency transceiver controller 7' are applied to the RF coils in the radiofrequency unit 7.

The control device 9 further comprises a saturation pulse determination unit 15, which is connected to the radiofrequency transceiver controller 7', and with which disclosed RF saturation pulses are ascertained that can be implemented by the radiofrequency unit 7. The control device 9 is overall designed to carry out a method in accordance with aspects of the disclosure.

A computing unit 13 comprised by the control device 9 is designed to execute all computing operations required for the necessary measurements and determinations. To this end required or hereby determined interim results and results can be stored in a memory unit S of the control device 9. The units represented should not hereby absolutely be understood to be physically separate units, but merely represent a subdivision into meaningful units, which however can also for example be implemented in fewer or even in just one single physical unit.

Control commands can be routed to the magnetic resonance system and/or results from the control device 9 such as e.g. image data can be displayed via an input/output device E/A of the magnetic resonance system 1, e.g. by a user.

A method described herein can also be present in the form of a computer program product which comprises a program and implements the described method on a control device 9 when it is executed on the control device 9. Likewise, an electronically readable data storage medium 26 with electronically readable control information stored thereon can be present which comprises at least one such computer program product as just described and is configured such that when the data storage medium 26 is used in a control device 9 of a magnetic resonance system 1 it carries out the described method.

The invention claimed is:

1. A method for actuating a magnetic resonance system having a radiofrequency (RF) unit designed to generate an RF pulse for saturation of nuclear spins in an area under examination of an object under examination, the method comprising:
    loading a B0 map of the magnetic resonance system;
    loading frequency information on nuclear spins to be saturated in the area under examination;
    ascertaining at least one global RF saturation pulse for global saturation of the nuclear spins to be saturated on the basis of the B0 map and the frequency information; and
    emitting the global RF saturation pulse via the radiofrequency unit of the magnetic resonance system, wherein the emitted global RF saturation pulse is adjusted in terms of time and space to static and/or dynamic magnetic field changes due to system-specific causes.

2. The method as claimed in claim 1, wherein the B0 map is measured only once, on installation of the magnetic resonance system.

3. The method as claimed in claim 1, wherein higher-order gradient-exemplar-specific disturbance terms are loaded, and the ascertainment of global RF saturation pulses takes the gradient-exemplar-specific disturbance terms into consideration.

4. The method as claimed in claim 3, wherein the gradient-exemplar-specific disturbance terms are measured only once, on startup of the magnetic resonance system.

5. The method as claimed in claim 1, wherein a protocol planned for an MR measurement is loaded and the ascertainment of global RF saturation pulses takes into consideration a characteristic time of the planned protocol.

6. The method as claimed in claim 1, wherein a global RF saturation pulse is ascertained only once, on startup of the magnetic resonance system.

7. The method as claimed in claim 1, wherein the radiofrequency unit has a plurality of transmission channels in signal connection with a plurality of transmission elements of the radiofrequency unit, and the RF saturation pulse has a plurality of components for the plurality of transmission channels.

8. A magnetic resonance system, comprising: a magnet unit; a gradient unit; a radiofrequency unit; and a controller with a radiofrequency transceiver controller and with an RF saturation pulse determination unit, wherein the controller is designed to execute a method as claimed in claim 1 on the magnetic resonance system.

9. A non-transitory electronically readable data storage medium with electronically readable control information stored thereon, which comprises at least one computer program and is configured such that when the data storage medium is used in a controller of a magnetic resonance system, it carries out a method as claimed in claim 1.

* * * * *